(12) United States Patent
Kaminski et al.

(10) Patent No.: US 7,381,555 B2
(45) Date of Patent: Jun. 3, 2008

(54) LACTOBACILLUS N-DEOXYRIBOSYL TRANSFERASES, CORRESPONDING NUCLEOTIDE SEQUENCES AND THEIR USES

(75) Inventors: Pierre-Alexandre Kaminski, Paris (FR); Patrick Tailliez, Casteineu le Lez (FR); Philippe Marliere, Etiolles (FR); Pascal Quenee, Maurepas (FR); Rachel Cotaya, Paris (FR)

(73) Assignees: Institut Pasteur, Paris (FR); Institut National de la Recherche Agronomique, Paris (FR)

( * ) Notice: Subject to any disclaimer, the term of this patent is extended or adjusted under 35 U.S.C. 154(b) by 57 days.

(21) Appl. No.: 11/097,292

(22) Filed: Apr. 4, 2005

(65) Prior Publication Data
US 2006/0068473 A1    Mar. 30, 2006

Related U.S. Application Data

(63) Continuation of application No. 10/488,248, filed as application No. PCT/FR02/03120 on Sep. 12, 2002, now abandoned.

(30) Foreign Application Priority Data
Sep. 14, 2001  (FR) .................................. 01 11911

(51) Int. Cl.
C07H 2/04   (2006.01)
C12N 9/10   (2006.01)
C12N 15/74  (2006.01)
C12N 1/21   (2006.01)

(52) U.S. Cl. .................. 435/193; 435/194; 435/252.3; 435/471; 435/193; 536/23.2

(58) Field of Classification Search ............... 435/69.3, 435/194, 252.3, 471, 193; 536/23.2
See application file for complete search history.

(56) References Cited

U.S. PATENT DOCUMENTS 6,087,132 A    7/2000  Vasiloiu

FOREIGN PATENT DOCUMENTS

| JP | 2002 051781 | 2/2002 |
| JP | 2002051781 | 2/2002 |
| WO | WO01/14566 | 3/2001 |

OTHER PUBLICATIONS

Armstrong S.R. et al. (Crystal structures of nucleoside 2-deoxyribosyltransferase in native and ligand-bound forms reveal architecture of the active site. Structure 4:97-107(1996)).*

Wolfgang Uerkvitz et al. Trans-N-deoxyribosylase from *Lactobacillus helveticus*, Crystallization and Properties. Eur. J. Biochemistry. 23(1971) 387-395.*

Danzin et al. Deoxyribosyl Transfer Catalysis with trans-N-Deoxyribosylase Kinetic Study of Purine(Pyrimidine) to Pyrimidine(Purine) trans-N-Deoxyribosylase Eur. J. Biochemistry. 62(1976) 255-262.*

Okuyama et al. (Molecular cloning and expression of the nucleoside deoxyribosyltransferase-II gene from *Lactobacillus helveticus*.; Biosci. Biotechnol. Biochem. 64:2243-2245 (2000) first appeared on Oct. 1, 2000.*

C. Danzin, et al., "Deoxyriboxyl Transfer Catalysts with trans-N-Deoxyribosylase," European Journal of Biochemistry, vol. 62, pp. 365-372. 1994.

J. Holguin, et al., "Trans-N-Deoxyribosylase, Purification by Affinity Chromatography and Characterization," Chemical Abstracts, indexes, American Chemical Society, Columbus, US, vol. 83, No. 7, p. 199. 1975.

K. Okuyama, et al., "Molecular Cloning and Expression of the Nucleoside Deoxyribosyltransferase-II Gene from *Lactobacillus Helveticus*," Bioscience Biotechnology and Biochemistry, 2000, vol. 64, No. 10, pp. 2243-2245.

XP 002240249 Abstract. Identification of the active site nucleophile in nucleoside 2-deoxyribosyltransferase as J. Biol. Chem. 270:15551-15556(1995).

P.A. Kaminski, "Functional Cloning, Heterologous Expression, and Purification of Two Different N-Deoxyribosyltransferases from *Lactobacillus Helveticus*," Journal of Biological Chemistry, Apr. 26, 2002, vol. 277, No. 17, pp. 14400-14407.

Steven A. Short, et al., "Active Site Amino Acids That Participate in the Catalytic Mechanism of Nucleoside 2'-Deoxyribosyltransferase", The Journal of Biological Chemistry, vol. 271, No. 9, Issue of Mar. 1, pp. 4978-4987 1996.

Holguin Jose, et al., Purification by affinity chromatography and characterization. 55084 z, Trans-N-deoxyribosylase (Serv. Biophys., CEN Saclay, Gif-sur—Yvette, Fr.) Eur. J. Biochem. 1975, 54(2), 505-14 (Eng.),XP 002044164 (Abstract only).

* cited by examiner

*Primary Examiner*—Rebecca E. Prouty
*Assistant Examiner*—Kagnew Gebreyesus
(74) *Attorney, Agent, or Firm*—Oblon, Spivak, McClelland, Maier & Neustadt, P.C.

(57) ABSTRACT

The invention concerns novel polypeptides and their fragments, isolated from *Lactobacillus*, having at least a N-deoxyribosyl transferase activity, the polynucleotides encoding said polypeptides, cloning and/or expression vectors including said polynucleotides, cells transformed by said vectors and specific antibodies directed against said polypeptides. The invention also concerns a method for enzymatic synthesis of deoxyribonucleosides.

9 Claims, No Drawings

LACTOBACILLUS N-DEOXYRIBOSYL TRANSFERASES, CORRESPONDING NUCLEOTIDE SEQUENCES AND THEIR USES

CROSS-REFERENCE TO RELATED APPLICATIONS

The present application is a continuation application of application Ser. No. 10/488,248 filed Mar. 11, 2004, now abandoned, which is a National State (371) of International Application PCT/FR02/03120, filed on Sep. 12, 2002, which claims priority to FR 01/11911, filed on Sep. 14, 2001.

The present invention relates to the field of biology, and more particularly to the microbiological production of base analogues. The present invention relates to new polypeptides and their fragments, isolated from *Lactobacillus*, having at least one N-deoxyribosyltransferase activity, the polynucleotides coding said polypeptides, the cloning and/or expression vectors including said polynucleotides, the cells transformed by said vectors and the specific antibodies directed against said polypeptides. The invention also relates to a process for enzymatic synthesis of deoxyribonucleosides.

The analogues of nucleosides the structure of which comprises alterations of the sugar or heterocyclic base, form a family of molecules active in the treatment of numerous bacterial, viral, parasitic and fungal infections as well as in antitumour chemotherapy [Périgaud et al., 1992]. Moreover the insecticidal and herbicidal properties of certain nucleoside antibiotics make them potential agents in the sector of agrichemicals and the environment [Isono, 1988]. The industry uses two methods for producing these analogues, organic synthesis and biocatalytic conversion (enzymatic conversion and microbiological conversion), which have advantages and, conversely, drawbacks. Organic synthesis makes it possible to achieve extremely widely varied chemical structures but requires multiple stages and is expensive in terms of reagents and solvents. On the other hand, the biocatalytic processes allow easy production in an aqueous medium but limited to a small number of possible compounds due to the specificity of the enzymes, which allow a limited range of analogues in the place of their physiological substrates. The phosphorylase nucleosides and N-deoxyribosyltransferase, which result from the purine and pyrimidine salvage pathways in the bacteria, are the enzymes most used for these enzymatic conversions (Krenisky et al., 1981).

There is therefore an urgent requirement to obtain enzymes for conversion of nucleosides and their derivatives, having a broadened enzyme activity in order to diversify the industrial production of these compounds. This is the technical problem which the inventors of the present invention propose to resolve.

The N-deoxyribosyltransferase of *Lactobacillus leichmannii* as well as that of *L. helveticus*, partially purified or not purified, is shown to be the best glycosyl group donor and tolerates a considerable number of structural variations on the base. This enzyme has been used for producing a certain number of analogues among which should be cited 2-chloro,2'-deoxyadenosine (Carson et al., 1984), 2',3'-dideoxynucleosides of natural bases (Carson and Wasson, 1988), or several pyrazolo(3,4-d)pyrimidine and triazolo(4,5-d)pyrimidine derivatives of 2',3'-dideoxycytidine and the corresponding base (Fischer et al., 1990).

With the aim of making available recombinant enzymes capable of treating the widest possible variety of deviant substrates either by the base or by the sugar, the inventors have isolated genes coding for an N-deoxyribosyltransferase activity of different strains of *lactobacilli*. This variety of N-deoxyribosyltransferase enzymes makes it possible to increase the chances of obtaining enzymes with specificity broadened by mutations in the wild-type genes or by chimeras of these wild-type genes.

Two classes of N-deoxyribosyltransferase have been distinguished (Danzin and Cardinaud, 1976), the first (Class I) designated ptd (for purine transdeoxyribosylase) catalyzing exclusively the exchange of deoxyribose between two purines:

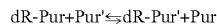

and the second (Class II) designated ntd (for nucleoside transdeoxyribosylase), the exchange of deoxyribose between a purine and a pyrimidine, between two pyrimidines or between two purines:

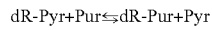

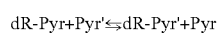

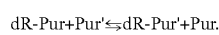

Only two genes specifying Class II enzymes, designated ntd, have been reported to date (Hück, 1997; dbj|BAA92683.2| (AB039914)).

A subject of the present invention is therefore an isolated or purified polypeptide of *Lactobacillus* having at least one N-deoxyribosyltransferase activity with a sequence of amino acids chosen from the sequences SEQ ID No.2, SEQ ID No.4, SEQ ID No.6, SEQ ID No.8, SEQ ID No.10, SEQ ID No.12, SEQ ID No.14.

According to a preferred embodiment, the polypeptide according to the invention is the N-deoxyribosyltransferase of SEQ ID No.2 (or SEQ ID No.14) coded by the ntd Lh gene of *Lactobacillus helveticus*.

According to a second embodiment, the polypeptide according to the invention is the N-deoxyribosyltransferase of SEQ ID No.4 coded by the ptd Lh gene of *Lactobacillus helveticus*.

According to a third embodiment, the polypeptide according to the invention is the N-deoxyribosyltransferase of SEQ ID No.6 coded by the ntd Lf gene of *Lactobacillus fermentum*.

According to a fourth embodiment, the polypeptide according to the invention is the N-deoxyribosyltransferase of SEQ ID No.8 coded by the ntd gene of *Lactobacillus crispatus*.

According to a fifth embodiment, the polypeptide according to the invention is the N-deoxyribosyltransferase of SEQ ID No.10 coded by the ntd gene of *Lactobacillus amylovorus*.

According to a sixth embodiment, the polypeptide according to the invention is the N-deoxyribosyltransferase of SEQ ID No.12 coded by the ntd gene of *Lactobacillus acidophilus*.

The isolated polypeptide according to the invention is characterized in that it comprises a polypeptide chosen from (a) a polypeptide of sequence SEQ ID No.2, SEQ ID No.4, SEQ ID No.6, SEQ ID No.8, SEQ ID No.10, SEQ ID No.12, SEQ ID No.14; (b) a polypeptide variant of a polypeptide with amino acid sequences defined in a); (c) a polypeptide homologous to the polypeptide defined in (a) or (b) and comprising at least 80% identity, preferably 85%, 87%, 90%, 95%, 97%, 98%, 99% identity with said polypeptide of a); (d) a fragment of at least 15 consecutive amino acids, preferably 17, 20, 23, 25, 30, 40, 50, 100, 250 consecutive amino acids of a polypeptide defined in a), b) or c); and (e) a biologically active fragment of a polypeptide defined in a), b) and c).

The polypeptide according to the invention is characterized in that it makes it possible to satisfy the guanine requirement of certain bacterial strains such as PAK6 which is a strain of *E. coli* the two genes of the guaBA operon of which, which control the conversion of IMP to XMP then to GMP, as well as those of the deoCABD operon which control the degradation of the deoxynucleosides, have been deleted. In fact, these strains, in order to survive or grow, require a supply of deoxyguanosine (dR-G) to the culture medium and the presence of a N-deoxyribosyltransferase activity of a polypeptide according to the invention in order to carry out the exchange: dR-G+A⇌dR-A+G.

In the present description, the term polypeptide will be used equally to designate a protein or a peptide.

By variant polypeptide is meant all of the mutated polypeptides which can exist naturally, in particular in the human being, and which correspond in particular to truncations, substitutions, deletions and/or additions of amino acid residues.

By homologous polypeptide is meant the polypeptides having, relative to the natural deoxyribosyltransferases of *Lactobacillus* according to the invention, certain modifications such as in particular a deletion, addition or substitution of at least one amino acid, a truncation, an elongation and/or chimeric fusion. Among the homologous polypeptides, those are preferred, the amino acid sequence of which has at least 80% identity, preferably at least 85%, 87%, 90%, 93%, 95%, 97%, 98%, 99% identity with the amino acid sequences of the polypeptides according to the invention. In the case of a substitution, one or more consecutive or non-consecutive amino acids can be replaced by "equivalent" amino acids. The expression "equivalent" amino acid is here intended to designate any amino acid capable of being substituted for one of the amino acids of the basic structure, without however modifying the characteristics or essential functional properties, such as their biological activities (i.e. of deoxyribosyltransferase), corresponding polypeptides such as the in vivo induction of antibodies capable of recognizing the polypeptide the amino acid sequence of which is comprised in the amino acid sequence SEQ ID No.2, SEQ ID No.4, SEQ ID No.6, SEQ ID No.8, SEQ ID No.10, SEQ ID No.12, SEQ ID No.14 or one of its fragments. These equivalent amino acids can be determined either on the basis of their homology of structure with the amino acids for which they are substituted, or on the basis of the results of tests for cross-species reactivity to which the different polypeptides are capable of giving rise. By way of example, there will be mentioned the possibilities of substitutions capable of being carried out without resulting in a more profound modification of biological activities of the corresponding modified polypeptides, the replacements, for example of leucine by valine or isoleucine, of aspartic acid by glutamic acid, of glutamine by asparagine, of arginine by lysine etc., it being naturally possible to envisage the reverse substitutions under the same conditions.

By polypeptide fragment is meant a polypeptide comprising at least 15 consecutive amino acids, preferably 17, 20, 23, 25, 30, 40, 50, 100, 250 consecutive amino acids. The polypeptide fragments according to the invention obtained by cleavage of said polypeptide by a proteolytic enzyme, by a chemical reagent, or by placing said polypeptide in a very acid environment, also form part of the invention.

By biologically active fragment is meant in particular a fragment of an amino acid sequence of a polypeptide according to the invention, having at least one of the characteristics or functional properties of the polypeptide according to the invention, in particular in that it comprises an N-deoxyribosyltransferase activity. The variant polypeptide, the homologous polypeptide or the polypeptide fragment according to the invention has at least 10%, preferably 20%, 30%, 40%, 50%, 60%, 70%, 80%, 90%, 95% of the N-deoxyribosyltransferase activity.

Different protocols known to a person skilled in the art have been described for introducing mutations into the polypeptides. Among these, there should be mentioned by way of example, the polymerase chain reaction (PCR) in the presence of manganese (Cadwell et al., 1992). The mutations can be introduced either randomly—in this case the mutagenesis stage is following by a stage of screening the mutant of interest—i.e. in targeted a manner. In the latter case, the mutations are preferably introduced at the level of the catalytic site of the N-deoxyribosyltransferases according to the invention.

Preferably a polypeptide according to the invention is a polypeptide constituted by the sequence SEQ ID No.2, SEQ ID No.4, SEQ ID No.6, SEQ ID No.8, SEQ ID No.10, SEQ ID No.12, SEQ ID No.14 or a sequence having at least 80%, preferably at least 85%, 90%, 95%, 98% and 99% identity with the SEQ ID No.2, SEQ ID No.4, SEQ ID No.6, SEQ ID No.8, SEQ ID No.10, SEQ ID No.12, SEQ ID No.14 after optimal alignment. By polypeptide the amino acid sequence of which having a percentage identity of least 80%, preferably at least 85%, 90%, 95%, 98% and 99% after optimal alignment with a reference sequence, is meant the polypeptides having certain modifications relative to the reference polypeptide, such as in particular one or more deletions, truncations, an elongation, a chimeric fusion, and/or one or more substitutions.

Among the polypeptides the amino acid sequence of which has a percentage identity of least 80%, preferably at least 0.85%, 90%, 95%, 98% and 99% after optimal alignment with the sequences SEQ ID No.2, SEQ ID No.4, SEQ ID No.6, SEQ ID No.8, SEQ ID No.10, SEQ ID No.12, SEQ ID No.14 or with one of their fragments according to the invention, the variant polypeptides coded by the variant peptide sequences as previously defined are preferred, in particular the polypeptides, the amino acid sequence of which has at least one mutation corresponding in particular to a truncation, deletion, substitution and/or addition of at least one amino acid residue relative to the sequences SEQ ID No.2, SEQ ID No.4, SEQ ID No.6, SEQ ID No.8, SEQ ID No.10, SEQ ID No.12, SEQ ID No.14 or with one of their fragments; more preferably, the variant polypeptides having at least one mutation which reduces the specificity of the polypeptide according to the invention for its substrate, such that the variant polypeptides according to the invention are capable of catalyzing a larger variety of substrate, in order to obtain a wider range of base analogues.

The invention also relates to a purified or isolated polynucleotide characerized in that it codes for a polypeptide as defined previously and preferably for a polypeptide of sequence SEQ ID No.2, SEQ ID No.4, SEQ ID No.6, SEQ ID No.8, SEQ ID No.10, SEQ ID No.12, SEQ ID No.14. Preferably, the polynucleotide according to the invention has the sequence SEQ ID No.1, SEQ ID No.3, SEQ ID No.5, SEQ ID No.7, SEQ ID No.9, SEQ ID No.11, SEQ ID No.13.

The isolated or purified polynucleotide according to the invention is characterized in that it comprises a polynucleotide chosen from (a) SEQ ID No.1, SEQ ID No.3, SEQ ID No.5, SEQ ID No.7, SEQ ID No.9, SEQ ID No.11, SEQ ID No.13; (b) the sequence of a fragment of at least 15 consecutive nucleotides, preferably at least 18, 21, 24, 27, 30, 35, 40, 50, 75, 100, 150, 200 consecutive nucleotides of the sequence SEQ ID No.1, SEQ ID No.3, SEQ ID No.5, SEQ ID No.7, SEQ ID No.9, SEQ ID No.11, SEQ ID No.13; (c) a nucleic sequence having a percentage identity of at least 70%, preferably at least 75%, 80%, 85%, 90%, 95%, 98%, 99% after optimal alignment with a sequence defined in a) or b); (d) the complementary sequence or the RNA sequence corresponding to a sequence as defined in a), b) or c).

The polynucleotide according to the invention is also characterized in that its expression in the host cells, in particular the bacterial strains such as PAK6, make it possible to satisfy the guanine requirement of said strain. The PAK6 strain was deposited at the CNCM, 28 rue du Docteur Roux 75724 Paris, France, on 2nd May 2001 under No. 1-2664. The PAK6 strain corresponds to the bacterial strain of *Escherichia coli* MG 1655 deleted of two guaA and guaB genes, as well as of the deoC, deoA, deoB, deoD genes. The PAK6 strain (ΔguaBA::gm Δdeo-11) is auxotrophic for guanine in minimal glucose medium.

By nucleic acid, nucleic sequence or nucleic acid sequence, polynucleotide, oligonucleotide, polynucleotide sequence, nucleotide sequence, terms which will be used interchangeably in the present description, is meant a precise chain of nucleotides, modified or unmodified, making it possible to define a fragment or a region of a nucleic acid, comprising or not comprising non-natural nucleotides, and being able to correspond equally well to a double-stranded DNA, a single-stranded DNA and transcription products of said DNAs, and/or a fragment of RNA.

It must be understood that the present invention does not relate to the nucleotide sequences in their natural chromosomal environment, i.e. in the natural state. They are sequences which have been isolated or purified, i.e. they have been collected, directly or indirectly, for example by copying, their environment having been at least partially modified. Thus the nucleic acids obtained by chemical synthesis are also meant.

By polynucleotide of complementary sequence is meant any DNA the nucleotides of which are those of SEQ ID No.1, SEQ ID No.3, SEQ ID No.5, SEQ ID No.7, SEQ ID No.9, SEQ ID No.11, SEQ ID No.13 or part of SEQ ID No.1, SEQ ID No.3, SEQ ID No.5, SEQ ID No.7, SEQ ID No.9, SEQ ID No.11, SEQ ID No.13, and the orientation of which is reversed.

By "percentage identity" between two nucleic acid or amino acid sequences within the meaning of the present invention, is meant a percentage of nucleotides or amino acid residues identical between the two sequences to be compared, obtained after the best alignment, this percentage being purely statistical and the differences between the two sequences being distributed at random and throughout their length. By "best alignment" or "significant alignment" is meant the alignment for which the percentage identity determined as follows is the highest. The comparisons of sequences between two nucleic acid or amino acid sequences are carried out in standard manner by comparing these sequences after having aligned them in significant manner, said comparison having been carried out by segment or by "window of comparison" in order to identify and compare the local regions of sequence similarity. The significant alignment of the sequences for the comparison can be carried out, apart from manually, by means of the local homology algorithm of Smith and Waterman (1981), by means of the local homology algorithm of Neddleman and Wunsch (1970), by means of the similarity search method of Pearson and Lipman (1988), by means of computer software using these algorithms (GAP, BESTFIT, BLAST P, BLAST N, FASTA and TFASTA in the Wisconsin Genetics Software Package, Genetics Computer Group, 575 Science Dr., Madison, Wis.). In order to obtain the significant alignment, the BLAST program is used, with the BLOSUM 62 matrix. The PAM or PAM250 matrices can also be used.

The percentage identity between two nucleic acid or amino acid sequences is determined by comparing these two sequences aligned in significant manner, the nucleic acid or amino acid sequence to be compared being able to comprise additions or deletions relative to the reference sequence for a significant alignment between these two sequences. The percentage identity is calculated by determining the number of identical positions for which the nucleotide or the amino acid residue is identical between the two sequences, by dividing this number of identical positions by the total number of positions compared and by multiplying the result obtained by 100 in order to obtain the percentage identity between these two sequences.

By nucleic sequences having a percentage identity of at least 70%, preferably at least 75%, 80%, 85%, 90%, 95%, 98% and 99% after significant alignment with a reference sequence, is meant the nucleic sequences having, relative to the reference nucleic sequence, certain modifications such as in particular a deletion, truncation, elongation, chimeric fusion, and/or a substitution, in particular a point substitution, and the nucleic sequence of which has at least 70%, preferably at least 75%, 80%, 85%, 90%, 95%, 98% and 99% identity after significant alignment with the reference nucleic sequence. These are preferably sequences the complementary sequences of which are capable of being hybridized specifically with the sequences SEQ ID No.1, SEQ ID No.3, SEQ ID No.5, SEQ ID No.7, SEQ ID No.9, SEQ ID No.11, SEQ ID No.13 of the invention. Preferably, the specific conditions of hybridization or of high stringency will be such that they ensure at least 70%, preferably at least 75%, 80%, 85%, 90%, 95%, 98% and 99% identity after significant alignment between one of the two sequences and the complementary sequence of the other. A hybridization under conditions of high stringency signifies that the conditions of temperature and ionic force are chosen in such a manner that they allow the maintenance of the hybridization between two fragments of complementary DNA. By way of illustration, conditions of high stringency of the hybridization stage for the purposes of defining the polynucleotide fragments described above, are advantageously the following: the DNA-DNA or DNA-RNA hybridization is carried out in two stages: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% formamide, 7% sodium dodecyl sulphate (SDS), 10×Denhardt's, 5% dextran sulphate and 1% salmon sperm DNA; (2) hybridization per se for 20 hours at a temperature depending on the size of the probe (i.e.: 42° C., for a probe of size >100 nucleotides) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C., for a probe of size >100 nucleotides). The hybridization conditions of high stringency described above for a polynucleotide of defined size, can be adapted by a person skilled in the art for oligonucleotides of a larger or smaller size, according to the teaching of Sambrook et al., 1989.

Among the nucleic sequences having a percentage identity of at least 70%, preferably at least 75%, 80%, 85%, 90%, 95%, 98% and 99% after significant alignment with the sequence according to the invention, the variant nucleic sequences of SEQ ID No.1, SEQ ID No.3, SEQ ID No.5, SEQ ID No.7, SEQ ID No.9, SEQ ID No.11, SEQ ID No.13 or their fragments are also preferred, i.e. all of the nucleic sequences corresponding to allelic variants, i.e. individual variations of the sequences SEQ ID No.1, SEQ ID No.3, SEQ ID No.5, SEQ ID No.7, SEQ ID No.9, SEQ ID No.11, SEQ ID No.13.

More particularly, the invention relates to a purified or isolated nucleic acid according to the present invention, characterized in that it comprises or is consituted by one of the sequences SEQ ID No.1, SEQ ID No.3, SEQ ID No.5, SEQ ID No.7, SEQ ID No.9, SEQ ID No.11, SEQ ID No.13, their complementary sequences or RNA sequences corresponding to SEQ ID No.1, SEQ ID No.3, SEQ ID No.5, SEQ ID No.7, SEQ ID No.9, SEQ ID No.11, SEQ ID No.13.

The primers or probes, characterized in that they comprise a nucleic acid sequence according to the invention, also form part of the invention. Thus, the primers or probes according to the invention are useful for the detection, identification, assay or amplification of the nucleic acid sequence. In particular, they can make it possible to demonstrate or distinguish between the variant nucleic sequences, or to identify the genome sequence of new eukaryotic or prokaryotic genes, in particular bacterial, and more precisely, of *Lactobacillus* bacteria, coding for an N-deoxyribosyltransferase, by using in particular an amplification method such as the PCR method, or a related method. According to the invention, the polynucleotides which can be used as probes or primers in processes for the detection, identification, assay or amplification of the nucleic sequence, have a minimal size of 10 bases, preferably at least 15, 18, 20, 25, 30, 40, 50 bases. According to one embodiment, the primers according to the invention are chosen from the sequences SEQ ID No.15 and SEQ ID No.16.

The polynucleotides according to the invention can thus be used as primers and/or probes in processes implementing in particular the PCR (polymerase chain reaction) technique (Rolfs et al., 1991). This technique requires the choice of pairs of oligonucleotide primers framing the fragment which has to be amplified. Reference can, for example, be made to the technique described in U.S. Pat. No. 4,683,202. The amplified fragments can be identified, for example according to agarose or polyacrylamide gel electrophoresis, or according to a chromatographic technique such as gel filtration or ion exchange chromatography, then sequenced. The specificity of the amplification can be controlled by using as primers the nucleotide sequences of polynucleotides of the invention and as matrices, plasmids containing these sequences or derived amplification products. The amplified nucleotide fragments can be used as reagents in hybridization reactions in order to demonstrate the presence, in a biological sample, of a target nucleic acid of sequence complementary to that of said amplified nucleotide fragments. The invention also relates to the nucleic acids capable of being obtained by amplification using primers according to the invention.

Other techniques for amplification of the target nucleic acid can be advantageously used as an alternative to the PCR (PCR-like) using primer pairs of nucleotide sequences according to the invention. By PCR-like is meant any methods implementing direct or indirect reproductions of the nucleic acid sequences, or in which the marking systems have been amplified, these techniques being of course known. Generally, it is a matter of amplification of the DNA by a polymerase; when the original sample is an RNA, reverse transcription should be carried out beforehand. There are currently very numerous processes allowing this amplification, for example the SDA (Strand Displacement Amplification) technique (Walker et al., 1992), the TAS (Transcription-based Amplification System) technique described by Kwoh et al. (1989), the 3SR (Self-Sustained Sequence Replication) technique described by Guatelli et al. (1990), the NASBA (Nucleic Acid Sequence Based Amplification) technique described by Kievitis et al. (1991), the TMA (Transcription Mediated Amplification) technique, the LCR (Ligase Chain Reaction) technique described by Landegren et al. (1988), the RCR (Repair Chain Reaction) technique described by Segev (1992), the CPR (Cycling Probe Reaction) technique described by Duck et al. (1990), the Q-β-replicase amplification technique described by Miele et al. (1983). Certain of these techniques have since been perfected.

In the case where the target polynucleotide to be detected is an mRNA, it is advantageous to use, prior to the implementation of an amplification reaction using primers according to the invention, or the implementation of a detection process using probes of the invention, a reverse transcriptase type enzyme in order to obtain a cDNA from the mRNA contained in the biological sample. The cDNA obtained will then serve as a target for the primers or probes used in the amplification or detection process according to the invention.

The probes hybridization technique can be carried out in various ways (Matthews et al. 1988). The most general method consists of immobilizing the nucleic acid extracted from the cells of different tissues or cells in culture on a support (such as nitrocellulose, nylon, polystyrene) in order to produce for example DNA chips, then incubating, under well defined conditions, the target nucleic acid immobilized with the probe. After the hybridization, the probe in excess is eliminated and the hybrid molecules formed are detected by the appropriate method (measurement of the radioactivity, fluorescence or enzyme activity linked to the probe).

According to another method of using nucleic probes according to the invention, the latter can be used as capture probes. In this case, a probe, called a "capture probe", is immobilized on a support and serves to capture by specific hybridization the target nucleic acid obtained from the biological sample to be tested and the target nucleic acid is then detected using a second probe, called a "detection probe", marked by an easily detectable element.

Among the fragments of useful nucleic acids, there should moreover be mentioned in particular the anti-sense oligonucleotides, i.e. the structure of which ensures, by hybridization with the target sequence, an inhibition of the expression of the corresponding product. Sense oligonucleotides should also be mentioned, which, by interaction with proteins involved in the regulation of the expression of the corresponding product, will induce either an inhibition, or an activation of this expression. The oligonucleotides according to the invention have a minimum size of 9 bases, preferably at least 10, 12, 15, 17, 20, 25, 30, 40, 50 bases.

The probes, primers and oligonucleotides according to the invention can be marked directly or indirectly by a radioactive or non-radioactive compound, by methods well known to a person skilled in the art, in order to obtain a detectable and/or quantifiable signal. The non-marked polynucleotide sequences according to the invention can be used directly as probes or primers.

The sequences are generally marked in order to obtain sequences which can be used for numerous applications. The marking of the primers or probes according to the invention is carried out by radioactive elements or by non-radioactive molecules. Among the radioactive isotopes used, there can be mentioned $^{32}P$, $^{33}P$, $^{35}S$, $^{3}H$, or $^{125}I$. The non-radioactive entities are selected from the ligands such as biotin, avidin, streptavidin, dioxygenin, haptens, colouring agents, luminescent agents such as the radioluminescent, chemoluminescent, bioluminescent, fluorescent, phosphorescent agents.

The invention also comprises a method for detection and/or assay of a polynucleotide according to the invention, in a biological sample, characterized in that it comprises the following stages: (i), isolation of the DNA from the biological sample to be analyzed, or obtaining of a cDNA from the RNA of the biological sample; (ii) specific amplification of the DNA coding for the polypeptide according to the invention using primers; (iii) analysis of the amplification products. A subject of the invention is also to provide a kit for the detection and/or assay of a nucleic acid according to the invention, in a biological sample, characterized in that it comprises the following elements: (i) a pair of nucleic primers according to the invention, (ii) the reagents necessary to carry out a DNA amplification reaction, and optionally (iii) a component making it possible to verify the sequence of the amplified fragment, more particularly a probe according to the invention.

The invention also comprises a method for detection and/or assay of a nucleic acid according to the invention, in a biological sample, characterized in that it comprises the following stages: (i) bringing a polynucleotide according to the invention into contact with a biological sample; (ii) detection and/or assay of the hybrid formed between said polynucleotide and the nucleic acid of the biological sample. A subject of the invention is also to provide a kit for the detection and/or assay of a nucleic acid according to the invention, in a biological sample, characterized in that it comprises the following elements: (i) a probe according to the invention, (ii) the reagents necessary for implementing a hybridization reaction, and/or, if appropriate, (iii) a pair of primers according to the invention, as well as the reagents necessary for a DNA amplification reaction.

Preferably, the biological sample according to the invention in which the detection and assay are carried out, is constituted by a culture medium, a cell homogenate, a body fluid, for example a human or animal serum, blood, milk.

The present invention also relates to the recombinant cloning and/or expression vectors comprising a polynucleotide according to the invention and/or expressing a polypeptide according to the invention. Such a host cell is also a subject of the invention.

Preferably, the recombinant vectors according to the invention are:

the vector called pLH2 comprising the polynucleotide SEQ ID No.1 as present in the bacterial strain deposited at the CNCM, 28 rue du Docteur Roux 75724 Paris, France, on 30 May 2001 under No. 1-2676; the pLH2 plasmid contains an AluI fragment of 1.4 kb containing the gene coding for the type II N-deoxyribosyltransferase of *Lactobacillus helveticus* CNRZ32 cloned in the SmaI site of the pBAM3 plasmid; the pLH2 plasmid, which expresses this enzyme, is propagated in the PAK6 strain which is auxotrophic for guanine;

the vector called pLH4 comprising the polynucleotide SEQ ID No.3 as present in the bacterial strain deposited at the CNCM, 28 rue du Docteur Roux 75724 Paris, France, on 30th May 2001 under No. I-2677; the pLH4 plasmid contains an AluI fragment of 1.6 kb containing the gene coding for the type I N-deoxyribosyltransferase of *Lactobacillus helveticus* CNRZ32 cloned in the SmaI site of the pBAM3 plasmid; the pLH4 plasmid, which expresses this enzyme, is propagated in the PAK6 strain which is auxotrophic for guanine;

the vector called pLF6 comprising the polynucleotide SEQ ID No.5 as present in the bacterial strain deposited at the CNCM, 28 rue du Docteur Roux 75724 Paris, France, on 30th May 2001 under No. I-2678; the pLF6 plasmid contains an AluI fragment of 1.36 kb containing the gene coding for the type II N-deoxyribosyltransferase of *Lactobacillus fermentum* CIP102780T. The pLF6 plasmid, which expresses this enzyme, is propagated in the PAK6 strain which is auxotrophic for guanine;

the vector called pLA comprising the polynucleotide SEQ ID No.11 as present in the bacterial strain deposited at the CNCM, 28 rue du Docteur Roux 75724 Paris, France, on 21st Jun. 2001 under No. I-2689; the pLA plasmid corresponds to the pSU19 plasmid, at the sites PstI and BamHI an insert is cloned containing the gene coding for the type II N-deoxyribosyltransferase of *Lactobacillus acidophilus* CNRZ 1296. The plasmid is propagated in the strain of *Escherichia coli* TG-I.

The vectors according to the invention comprise the elements necessary for the expression and in particular, preferably a promoter, of the translation initiation and termination signals, as well as appropriate regions for regulation of the transcription. They must be able to be maintained in stable fashion in the cell and can optionally have particular signals specifying the secretion of the translated protein.

The different control signals are chosen as a function of the host cell used. To this end, the nucleic acid sequences according to the invention can be inserted into autonomous replication vectors inside the chosen host, or integrative vectors of the chosen host. Among the autonomous replication systems, as a function of the host cell, "plasmid", "cosmid", "phagemid" or "mini-chromosome" type systems or viral type systems are preferably used, the viral vectors being able in particular to be adenoviruses (Perricaudet et al., 1992), retroviruses, lentiviruses, poxviruses, or herpetic viruses (Epstein et al., 1992). A person skilled in the art knows the technologies which can be used for each of these systems. When it is desired to integrate the sequence into the chromosomes of the host cell, it is possible to use, for example, plasmidic or viral type systems; such viruses are, for example, the retroviruses (Temin, 1986), or the AAVs (Carter, 1993).

Among the non-viral vectors, naked polynucleotides such as naked DNA or naked RNA are preferred according to the technique developed by VICAL, the bacterial artificial chromosomes (BACs), yeast artificial chromosomes (YACs) for expression in yeast, mouse artificial chromosomes (MACs) for expression in murine cells and in preferred manner human artificial chromosomes (HACs) for expression in human cells.

Such vectors are prepared according to the methods currently used by a person skilled in the art and the resultant clones can be introduced into an appropriate host by standard methods, such as for example lipofection, electroporation, heat shock, transformation after chemical permeabilization of the membrane, cell fusion.

The invention comprises moreover the host cells, in particular the eukaryotic and prokaryotic cells transformed by the vectors according to the invention. Among the cells which can be used within the meaning of the present invention, bacteria and yeasts can be mentioned. According to a preferred embodiment of the invention, the bacterium is chosen from the group composed of *Lactobacillus fermentum, Lactobacillus acidophilus, Lactobacillus amylovorus, Lactobacillus crispatus, Lactobacillus helveticum, Lactobacillus lactis, Escherichia coli, Bacillus subtilus, Campylobacter pylori, Helicobacter pylori, Agrobacterium tumefaciens, Staphylococcus aureus, Thermophilus aquaticus, Azorhizobium caulinodans, Rhizobium leguminosarum, Neisseria gonorrhoeae, Neisseria meningitis*. According to a preferred embodiment of the invention, the bacterium is *Lactobacillus*. According to a preferred embodiment it is:

the bacterium transformed by the pLH2 plasmid comprising the polynucleotide SEQ ID No.1, as deposited at the CNCM on 30 May 2001 under No. I-2676;

the bacterium transformed by the pLH4 plasmid comprising the polynucleotide SEQ ID No.3, as deposited at the CNCM on 30 May 2001 under No. I-2677;

the bacterium transformed by the pLF6 plasmid comprising the polynucleotide SEQ ID No.5, as deposited at the CNCM on 30 May 2001 under No. I-2678;

the bacterium transformed by the pLA plasmid comprising the polynucleotide SEQ ID No.11, as deposited at the CNCM on 21st June under No. I-2689;

According to another preferred embodiment the bacterium is *Escherichia coli*. According to another embodiment of the invention, the cell is a yeast which is preferably *Saccharomyces cerevisiae, Saccharomyces pombe, Candida albicans*.

Among the host cells according to the invention, there should also be mentioned the cells of insects, animal or plant cells.

Preferably, the cell according to the invention is free from any enzyme activity capable of degrading said precursor deoxyribonucleoside or said deoxyribonucleoside obtained by bioenzymatic reaction catalyzed by a polypeptide according to the invention. Alternatively, said host cell can be free from additional bioenzymatic activities intended to transform the precursor deoxyribonucleoside and/or deoxyribonucleoside obtained by the bioenzymatic reaction catalyzed by the polypeptide according to the invention. Among these additional bioenzymatic activities, there should be mentioned phosphorylation, sulphatation, acetylation, succinylation, methylation.

The nucleic acid sequence coding for the N-deoxyribosyltransferases according to the invention is either naturally present in said cell or is introduced into said cell by the recombinant DNA techniques known to a person skilled in the art. According to a preferred embodiment, the nucleic acid sequence introduced into said cell by the recombinant DNA techniques and which codes for an N-deoxyribosyltransferase according to the invention is heterologous. By heterologous nucleic acid sequence is meant a nucleic acid sequence which is not naturally present in the cell according to the invention.

The present invention also relates to metazoic, plant or animal organisms, preferably mammals, except humans, comprising one of said cells transformed according to the invention. Among the animals according to the invention, rodents are preferred, in particular mice, rats or rabbits, expressing at least one polypeptide according to the invention.

The cells, preferably bacterial, or fungal, in particular of yeast, as well as the metazoic organisms according to the invention can be used in a method for producing N-deoxyribosyltransferase according to the invention. The method for producing a polypeptide of the invention in recombinant form, itself included in the present invention, is characterized in that the transformed cells are cultured, in particular the cells of the present invention, under conditions allowing the expression and optionally the secretion of a recombinant polypeptide coded by a nucleic acid sequence according to the invention, and said recombinant polypeptide is recovered. The recombinant polypeptides capable of being obtained by this production method also form part of the invention. They can be presented in glycosylated or non-glycosylated form, and may or may not have the tertiary structure of the natural protein. The recombinant polypeptide sequences can also be modified in order to improve their solubility, in particular in aqueous solvents. Such modifications are known to a person skilled in the art such as for example the deletion of hydrophobic domains or the substitution of hydrophobic amino acids by hydrophilic amino acids.

These polypeptides can be produced from the nucleic acid sequences defined above, according to the techniques for producing recombinant polypeptides known to a person skilled in the art. In this case, the nucleic acid sequence used is placed under the control of signals allowing its expression in a host cell.

An effective system for producing a recombinant polypeptide requires a vector and a host cell according to the invention. These cells can be obtained by the introduction into host cells of a nucleotide sequence inserted into a vector as defined above, then the culture of said cells under conditions allowing the replication and/or expression of the transfected nucleotide sequence.

The processes used for purifying a recombinant polypeptide are known to a person skilled in the art. The recombinant polypeptide can be purified starting with lysates and cell extracts, culture medium supernatant, by methods used individually or in combination, such as fractionation, chromatography methods, immunoaffinity techniques using specific monoclonal or polyclonal antibodies, etc. A preferred variant consists of producing a recombinant polypeptide fused to a "carrier" protein (chimera protein). The advantage of this system is that it allows a stabilization and reduction of the proteolysis of the recombinant product, an increase in solubility during in vitro renaturation and/or simplification of the purification when the fusion partner has an affinity for a specific ligand.

The polypeptides according to the present invention can also be obtained by chemical synthesis using one of the numerous known peptide syntheses, for example the techniques using solid phases or techniques using partial solid phases, by condensation of fragments or by a synthesis in standard solution. The polypeptides obtained by chemical synthesis and being able to comprise corresponding non-natural amino acids are also included in the invention.

The polypeptides according to the invention make it possible to prepare monoclonal or polyclonal antibodies. It is therefore also one of the subjects of the present invention to provide a monoclonal or polyclonal antibody and its fragments, characterized in that they selectively and/or specifically bind a polypeptide according to the invention. The chimeric antibodies, humanized antibodies and single-chain antibodies also form part of the invention. The antibody fragments according to the invention are preferably Fab, F(ab')2, Fc or Fv fragments. The polyclonal antibodies can be prepared, for example by immunization of an animal, in particular a mouse, with a polypeptide according to the invention combindd with an immune response adjuvant, then purification of the specific antibodies contained in the serum of the animals immunized on an affinity column on which the polypeptide having served as antigen has been fixed beforehand. The polyclonal antibodies according to the invention can also be prepared by purification on an affinity column on which a polypeptide according to the invention has been immobilized beforehand. The monoclonal antibodies can advantageously be prepared from hybridomas according to the technique described by Kohler and Milstein in 1975.

According to a particular embodiment of the invention, the antibody is capable of inhibiting the interaction between the N-deoxyribosyltransferase of the invention and its substrate in order co alter the physiological function of said N-deoxyribosyltransferase polypeptide.

The invention also relates to methods for the detection and/or purification of a polypeptide according to the invention, characterized in that they use an antibody according to the invention. The invention moreover comprises purified polypeptides, characterized in that they are obtained by a method according to the invention.

Moreover, apart from their use for the purification of the polypeptides, the antibodies of the invention, in particular the monoclonal antibodies, can also be used for the detection of these polypeptides in a biological sample.

For these different uses, the antibodies of the invention can also be marked in the same manner as described previously for the nucleic probes of the invention and in preferred manner with an enzymatic, fluorescent or radioactive marking.

The antibodies of the invention also constitute a means of analysis of the polypeptide expression according to the invention, for example by immunofluorescence, marking with gold, enzyme immunoconjugates. More generally, the antibodies of the invention can be advantageously used in any situation where the expression of a polypeptide according to the invention, normal or mutated, must be observed, and more particularly in immunocytochemistry or immunohistochemistry or in "western" blotting experiments. Thus, a process for detecting a polypeptide according to the invention in a biological sample, comprising the stages of bringing the biological sample into contact with an antibody according to the invention and demonstrating the antigen-antibody complex formed is also a subject of the invention.

It is also one of the subjects of the present invention to provide a process for in vitro or in vivo enzymatic synthesis of deoxyribonucleotides characterized in that it comprises at least one reaction stage catalyzed by at least one N-deoxyribosyltransferase according to the invention. The process according to the invention is characterized in that said N-deoxyribosyltransferase catalyzes the exchange of a first nucleobase present in a deoxyribonucleoside by a second nucleobase.

According to a preferred embodiment of the invention, said second nucleobase is selected from the group composed of the purines bound by N9, pyrimidines bound by N1, azines bound by N1, imidazoles bound by N1, said second nucleobases being able to carry substitutions of the hydrogens at the non-bound positions. Preferably, said second nucleobase is selected from the group composed of 6-methyl purine, 2-amino-6-methylmercaptopurine, 6-dimethylaminopurine, 5-azacytidine, 2,6-dichloropurine, 6-chloroguanine, 6-chloropurine, 6-aza-thymine, 5-fluoro-uracile, ethyl-4-amino-5-imidazole carboxylate, imidazole-4-carboxamide and 1,2,4-triazole-3-carboxamide.

Said first nucleobase is itself preferably selected from the group composed of adenine, guanine, thymine, uracile and hypoxanthine. These lists are not exhaustive, and it is evident that natural or non-natural analogues of nucleobases can be used in the present invention as substrate of an N-deoxyribosyltransferase of the invention.

Optionally, the in vivo process according to the invention is characterized in that it moreover comprises the stage of introducing into the host cell the first nucleobase present in a deoxyribonucleoside.

Optionally, the in vivo process according to the invention is characterized in that it moreover comprises the stage of introducing into the host cell the second nucleobase present in a deoxyribonucleoside.

Optionally, the in vivo process according to the invention is characterized in that it moreover comprises the stage of introducing to the host cell the first nucleobase present in a deoxyribonucleoside and the second nucleobase simultaneously and/or one after the other.

The deoxyribonucleosides capable of being produced in large quantities and inexpensively by the biosynthesis method according to the invention therefore constitute compounds of interest intended for the preventive or curative treatment of human or animal, tumorous, viral pathologies such as AIDS (acquired human immunodeficiency syndrome), bacterial, parasitic or fungal pathologies. Alternatively, these deoxyribonucleosides capable of being produced in large quantities and inexpensively by the biosynthesis method according to the invention constitute herbicides and insecticides.

The present invention also provides a process for nutritional screening intended to isolate deoxyribosyltransferases, preferably the polypeptides according to the invention but also their homologues or their mutants. This first screening according to the invention comprises the stages:

(i) (optionally) obtaining a bacterial strain, such as *Escherichia coli*, auxotrophic for guanine. Preferably this strain is incapable of growing in the presence of deoxyguanosine as a source of guanine. In preferred manner, it is the PAK 6 strain.

(ii) transfer of exogenous DNA, preferably in the form of an expression vector, into the bacterium, the exogenous DNA being capable of comprising a sequence coding for a deoxyribosyltransferase.

(iii) culture of the bacteria obtained in Stage (ii) on a medium containing deoxyguanosine.

(iv) isolation of the exogenous DNA transferred into the bacteria of Stage (iii) which have developed on the medium containing deoxyguanosine.

The present invention also provides a nutritional screening for distinguishing the deoxyribosyltransferase I and II activities, preferably in particular for distinguishing between the ntd and ptd polypeptides according to the invention. This second screening comprises the stages of:

(i) obtaining a bacterial strain such as for example *Escherichia coli*, auxotrophic for guanine and thymidine. Preferably, this strain is incapable of growing in the presence of guanine and thymidine. In preferred manner, it is the PAK 26 strain (ΔguaBguaA::Δdeo-11ΔthyA::ermΔ(udp-metE)zif9::Tn10) is auxotrophic for methionine, guanine and thymidine.

(ii) transfer of the exogenous DNA, preferably in the form of an expression vector, into the bacterium, the exogenous DNA being capable of comprising a sequence coding for a deoxyribosyltransferase I or II.

(iii) culture of the bacteria obtained in Stage (ii) on a medium containing deoxyguanosine, then determination of whether the bacteria are growing or not. If the bacteria are growing, then the exogenous DNA codes for a deoxyribosyltransferase II activity which is expressed in said bacterium. If the bacteria are not growing, then the exogenous DNA is capable of coding for a deoxyribosyltransferase I activity.

Other characteristics and advantages of the invention are clear from the rest of the description, with examples represented hereafter.

EXAMPLES

1. Material and Methods

1.1 Strains and Culturing Conditions

The strains of lactic bacteria used originate from the CNRZ (Centre National de Recherche Zootechnique) collection, Unité de Recherches Laitières et Génétique Appliquée, INRA, Jouy en Josas. They are cultured in MRS medium (from Man et al., J. Appl. Bacteriol., 23: 130-135, 1960) and incubated at 30° C., 37° C. or 42° C. according to the species. The *Escherichia coli* TG1 strain, provided by Stratagène, is cultured in LB (Luria broth base 10 g/L, Agar-agar 16 g/L) under agitation and at 37° C.

1.2. Preparation of Total Cellular DNA of Lactic Bacteria:

The cultures at the end of the exponential phase are centrifuged for 5 minutes at 13,000 g. The pellet corresponding to a culture of 2 ml is taken up in 200 µl of TES (50 mM Tris, pH8, 10 mM EDTA, pH8, 250 mM saccharose) containing 20 µg/ml of lysozyme and 50 U/ml of mutanolysine (Sigma). After an incubation of one hour at 37° C., the clarification of the preparation is obtained by adding 60 µl of 20% SDS.

The extraction of the nucleic acids is carried out by adding to the lysate 500 µl of saturated phenol in water, pH8, to which 0.1% hydroxyquinoline and 100 µl of a mixture of isoamylic chloroform-alcohol (24/1, V/V) has been added. The solution is homogenized then centrifuged for 10 minutes at 13,000 g and at ambient temperature. The upper, limpid phase containing the nucleic acids is retained. The extraction is repeated three times on the latter in order to eliminate the undesired cellular constituents. The phenol traces are eliminated by adding 500 µl of isoamylic chloroform-alcohol to the aqueous phase. After homogenization and centrifuging for 3 minutes at 15,000 g and at 4° C., the nucleic acids contained in the upper aqueous phase are precipitated by the addition of a volume of cold isopropanol. After an incubation of one hour at −20° C., a centrifugation is carried out for 20 minutes at 15,000 g and at 4° C. The isopropanol is eliminated and replaced by 500 µl of 70% ethanol. A final centrifugation of 10 minutes at 15,000 g and at 4° C. allows a pellet of nucleic acids to be recovered. This is left to dry in an evaporator and resuspended in 200 µl of sterile water containing 10 µl of RNase at 10 µg/µl. After 15 minutes of incubation at 37° C. to agitate the enzyme degrading the RNAs, 10 µl of the DNA solution is migrated by electrophoresis in an 0.8% agarose gel in order to evaluate the concentration and the quality.

1.3. Polymerase Chain Reaction of DNA (PCR):

Polymerase chain reactions (PCR) are carried out in a reaction volume of 100 µl containing 20 to 100 ng of DNA, 0.5 µM primers, 200 µM dNTPs (DATP, dCTP, dGTP, dTTP) in a 10 mM Tris-HCl buffer pH 9, 50 mM KCl, 1.5 mM MgCl$_2$, 0.002% BSA as well as 2.5 units of Taq polymerase. Thirty amplification cycles were used (Gene Amp PCR systems 2400, Perkin Elmer). The inventors defined two ntd1 (SEQ ID no. 15) and ntd2 primers (SEQ ID no. 16) starting from the ntd sequence of *Lactobacillus leichmanii* described by Huck (personal communication):

1.4. Southern-type Hybridization:

Enzymatic restriction of the DNAs. The total DNAs are digested by one or more restriction enzymes. The enzymes used are: BamHI, BglII, ClaI, EcoRI, HindIII, HpaI, NcoI, NotI, PstI, XbaI, XhoI (Bio-Lab). Digestion is carried out in a final volume of 40 µl containing 70 U of enzyme, 4 µl of 10×NEB buffer (Bio-Lab) and 4 to 8 µg of DNA. The incubation is carried out for 1 hour 30 minutes at 37° C.

Transfer of the DNA to a membrane. The total DNA fragments resulting from the enzymatic digestion are separated using a 0.7% agarose gel. After migration, the agarose gel is placed under agitation in a depurination solution (0.25N HCl) for 30 minutes. This process thus allows the transfer of DNA fragments larger than 10 kbs. After rinsing with water, the DNA is denatured by placing the gel for 40 minutes into a solution of 5M NaCl, 0.5M NaOH. The gel is rinsed with water then incubated again for 30 minutes in a neutralization solution, 1.5M NaCl, 0.5M Tris HCl; pH 7.5. The DNAs are transferred by capillarity onto a positively charged nylon membrane (Hybond N+, Amersham). They are eluted by a rising flux of 20×SSC (0.3M trisodium citrate; 3M NaCl; pH7). After the transfer, the DNAs are covalently bound onto the membrane using a UV Stratalinker 2400 apparatus (Stratagene).

Preparation of the probe. The probe used is an internal fragment of the ntd gene of *Lactobacillus helveticus* amplified by PCR. The probe is purified using the Wizard kit (Promega) in order to eliminate the PCR primers. The necessary concentration of the probe is 10 ng/µl. The DNA is marked using the ECL marking kit (Amersham). To do this, the DNA is denatured by heating for 5 minutes at 100° C. and immediately recooled in ice. A volume of marking reagent (peroxidase) then a volume of glutaraldehyde solution are added. This solution is incubated for 10 minutes at 37° C. for covalently binding the peroxidase to the DNA.

Hybridization and development. After a prehybridization of one hour at 42° C. in hybridization buffer, the membrane is hybridized for 16 hours at 42° C. in the presence of the marked probe. In order to eliminate the probe bound in non-specific manner, the membrane is washed for 20 minutes at 42° C. in two successive baths of buffer: 6M urea-0.4% SDS-0.5×SSC, then rinsed for 5 minutes in two successive baths of buffer: 0.3M sodium citrate-3M NaCl pH 7. The development is carried out by autoradiography according to the protocol of the ECL kit. A first development reagent containing hydrogen peroxide is reduced by peroxidase bound to the probe. Then the luminol contained in a second development reagent is oxidized, producing light which exposes the autoradiographic film.

1.5. Cloning the PCT Fragments:

The homologous ntd genes amplified by PCR are inserted into the plasmid vector pBluescript II SK+ of *E. coli*. TG1 (Stratagene). This plasmid is first restricted in its single site by the EcoRV enzyme (Gibco-BRL) which creates free ends. The digestion mixing is carried out in a volume of 30 µl, containing 4 µl of DNA. The DNA fragments amplified to be cloned should have their 5' and 3' ends free in order to

```
ntd1    5'-AGA CGA TCT ACT TCG GTG-3'    18 bases    Tm = 54° C.

ntd2    5'-ACG GCA CCT TCG TAG AAG-3'    18 bases    Tm = 56° C.
``` allow cloning. The preparation of the free ends of 50 µl of PCR products purified using the Wizard kit (Promega) is carried out in a reaction volume of 100 µl containing 3.6 units of polymerase DNA of the T4 phage (Bio-Lab) and 6 units of polymerase I DNA (or Klenow fragment) (Bio-Lab), not having a 5'>3' exonucleic activity. The polymerization is carried out for 20 minutes at 11° C. then the enzymes are deactivated after 10 minutes at 75° C. The DNA is then precipitated in the presence of two volumes of 100% ethanol, glycogen and 10% 3M sodium acetate, pH 4.8. The mixture is placed for one hour at −20° C. then centrifuged for 20 minutes at 15,000 g. The pellet is rinsed with 250 µl of 70% ethanol, centrifuged again for 10 minutes at 15,000 g, dried in an evaporator and resuspended in 20 µl of sterile water.

The DNA restricts the pBS-SK+ plasmid and the amplified fragment is comigrated on a 0.7% agarose gel in order to evaluate their respective concentrations: the number of molecules of the fragment to be cloned should be three to four times greater than that of the plasmid. The ligation is carried out in a volume of 10 µl containing 60 ng of insert, 26 ng of restricted pBS-SK+ plasmid, 2 units of ligase (T4 DNA ligase, Boehringer-Mannheim), overnight at 16° C. The ligation products are dialyzed on a 0.025 µm millipore filter so as to eliminate the salts and to thus avoid electric arcs during electroporation.

1.6. Transformation:

Preparation of electrocompetent cells of the TG1 strain of *E. coli*. Starting from 5 ml of an overnight culture at 37° C. under agitation, 500 ml of LB medium are inoculated. The culture is placed under agitation at 37° C. until an $O.D._{600\ nm}=1$ is reached. It is then recooled for 2 hours in ice then cold-centrifuged for 10 minutes at 5,000 rpm. The supernatant is eliminated, the pellet is taken up in 400 ml of cold water. This preparation is cold-centrifuged for 10 minutes and at 5,000 rpm. The pellet obtained is taken up again in 250 ml of cold water. Following a centrifugation of 10 minutes, the pellet is taken up in 25 ml of cold water then the cells are suspended in a final volume of 1 ml of 10% glycerol, and aliquotted before being rapidly frozen in liquid nitrogen.

Transformation by electroporation and selection of clones. The electrocompetent cells preserved at −80° C. are thawed in ice then brought into contact with 5 µl of ligature mixture in an electroporation flask. The Gene-Pulser (Bio-Rad) is regulated at 200 volts, 25 mF, 250 ohms. The cells are then subjected to electroporation. 1 ml of an SOC solution is added (20 g/L bactopeptone, 5 g/L yeast extract, 2 ml/L 5M NaCl, 2.5 ml/L 1M KCl, 10 ml/L 1M $MgCl_2$, 10 ml/L 1M $MgSO_4$), containing 0.4% glucose in cell suspension which is incubated at 37° C. for one hour. The cells are then plated on an LB selective medium −Xgal (5-bromo-4-chloro-3-indolyl-β-D-galactoside, 1 µg/ml)-IPTG (isopropythio-β-D-galactoside, 1 µg/ml)-ampicillin (50 µg/ml) and incubated at 37° C. overnight.

Rapid extraction of plasmidic DNA of recombinant *E. coli* clones by alkaline lysis. The *E. coli* cells transformed and cultivated in LB medium containing ampicillin (100 µg/ml) are harvested by centrifugation at 15,000 for 10 minutes at 4° C. They are resuspended in 100 µl of a 50 mM saccharose solution, 25 mM Tris-HCl, pH 8, 10 mM EDTA, pH 8. The alkaline lysis and the denaturation of the DNA is carried out by addition of 200 µl 0.2N NaOH, 1% SDS. The reaction medium is left for 1 minute at ambient temperature after having added 200 µl of chloroform. Then 150 µl of a solution of 5M potassium acetate, glacial acetic acid are added. The reaction medium is centrifuged for 15 minutes at 13,000 g at 4° C. The aqueous phase containing the DNA is precipitated in the presence of 2 volumes of 100% ethanol then centrifuged for 20 minutes at 13,000 g at 4° C. The pellet is washed in 70% ethanol, centrifuged for 10 minutes at 13,000 g then resuspended in 30 µl of sterile water containing RNase at 10 ng/ml.

1.7. Inverse PCR

Inverse PCR allows the regions flanking a fragment of DNA of known sequence to be amplified. This technique takes place in three steps:

Digestion of the DNA matrix. The DNA matrix is digested by one or two restriction enzymes chosen such that they do not cleave in the known gene sequence and they allow a fragment of suitable size (1 to 3 kb) to be obtained. To choose a suitable enzyme, the total DNA is digested separately by several enzymes. Then Southern-type hybridizations are carried out using the DNA fragment of known sequence as a probe. The digestions for which the probe hybridizes with a fragment of 1 to 3 kb are used for the inverse PCR. The DNA fragments obtained by digestion are circularized. For this purpose, 100 units of T4 DNA ligase and 100 µl of ligation buffer are added to 4 to 8 µg of DNA in a final volume of 1 ml. The ligation mixture is incubated at 15° C. overnight. The ligated DNA is then precipitated with 100 µl of 3M sodium acetate, pH 4.8, 700 µl of isopropanol and 2 µl of glycogen, then centrifuged for 30 minutes at 13,000 g at 4° C. The pellet is rinsed in 300 µl of 70% ethanol and centrifuged for 10 minutes at 13,000 g at 4° C. The pellet is taken up in 25 µl of ultrapure water.

Amplification of circularized DNAs using different primers. The polymerase chain reactions are carried out in a reaction volume of 100 µl containing 20 to 100 ng of DNA, 0.5 µM primers, 200 µM dNTPs (dATP, dCTP, dGTP, dTTP) in a 10 mM Tris-HCl buffer pH 9, 50 mM KCl, $MgCl_2$ with 1.5 mM BSA at 0.002% and 2.5 units of Taq polymerase.

The amplification is carried out under the following conditions:

| | | |
|---|---|---|
| 94° C. | 3 minutes | |
| 94° C. | 30 seconds | 25 cycles |
| 50 to 60° C. (according to the Tm of the primers used) | 1 minute | |
| 72° C. | 3 minutes | |
| (Gene Amp PCR systems 2400, Perkin Elmer). | | |

Sequencing. The PCR fragments are purified by the Wizard kit (Promega) in order to eliminate the non-incorporated oligonucleotides, the salts and the Taq polymerase. The sequencing is carried out using a 373A automatic sequencer (Applied Biosystems-Perkin Elmer) using an ABI PRISM Dye Terminator kit (Perkin Elmer) based on the incorporation of fluorescent phosphate deoxynucleotides during the elongation phase of the primers. The sequence reactions are carried out in a reaction volume of 20 µl containing 30 ng of DNA, 4 µl of DyeT Mix (Perkin Elmer Biosystems) and 0.1 mM of primer.

| Cycle: | | |
|---|---|---|
| 96° C. | 1 minute | |
| 96° C. | 10 seconds | 25 cycles |
| 50° C. | 5 seconds | |
| 60° C. | 4 minutes | |

20 µl of 3M sodium acetate, pH 4.6, 50 µl of 95% ethanol and 1 µl of glycogen are added to each sequence reaction. The solution is left for 15 minutes at ambient temperature then centrifuged for 20 minutes at 13,000 g. The pellet is then rinsed with 250 µl of 70% ethanol then centrifuged for 10 minutes at 13,000 g. The pellet is then taken up in 6 µl of sequence blue (83% formamide, 8.3 mM EDTA, 0.5% dextran blue 2,000,000 (Sigma)). The samples are denatured for 3 minutes at 90% and 3 µl deposited on 4% acrylamide gel.

2. A Single Nutritional Screening for the Two Classes of N-Deoxyribosyltransferase in *Escherichia Coli*

A functional screening allowing the production of guanine to be selected was established on *E. coli* by deleting the two genes of the guaBA operon which controls the conversion of IMP into XMP then into GMP and also those of the deoCABD operon which controls the degradation of deoxynucleosides to give the PAK 6 strain. The *E. coli* genome specifies an activity allowing the base G to be converted into GMP (guanine phosphoribosyltransferase encoded by the gpt gene), and also an activity allowing the base G to be released from the dR-G deoxynucleoside (purine nucleoside phosphorylase encoded by the deoD gene in the deo operon). The PAK 6 strain thus has a requirement for guanine (G) which cannot be satisfied by the addition of deoxyguanosine (dR-G). The use of deoxyguanosine (dR-G) can however be selected if an N-deoxyribosyltransferase activity is expressed in the PAK6 strain in order to carry out the exchange: dR-G+A⇌dR-A+G.

This exchange between two purine bases can be catalyzed by the two enzyme classes. In fact, the introduction of the ntd gene of *L. leichmannii* into the PAK 6 strain allows the requirement for guanine to be satisfied using deoxyguanosine (dR-G) and adenine (A)

3. Functional Cloning of the PDT Gene of *L. Helveticus*

DNA fragments of a size comprised between 1 and 2 kb obtained by partial digestion (AluI) of *L. helveticus* CNRZ 32 were ligated in a ColE1 plasmid (of pUC type digested by SmaI and desphosphorylated) and the mixture is used to transform the PAK6 strain. The transforming clones were selected in a glucose mineral medium to which deoxyguanosine (dR-G) and adenine (A) have been added to the final concentration of 0.3 mM.

One of the transforming clones proved to propagate a plasmid containing an insert controlling a Class I N-deoxyribosyltransferase activity and deviating from the restriction profile of the ntd gene of *L. helveticus*. The sequence of this insert develops a gene specifying a polypeptide of 167 amino acids with a molecular weight of 18790.70 Daltons having a similarity of 28.6% with the NTD polypeptide of *L. leichmanii*. The sequence of this gene called ptd deviates from that of the ntd genes making them impossible to hybridize (7.5% identity).

Incidentally the ntd gene of *L. helveticus* controlling a Class II N-deoxyribosyltransferase activity could be isolated once again among the transforming clones selected.

4. Functional Cloning of the NTD Gene of *L. Fermentum*

The same nutritional cloning and selection operations were carried out starting from genomic DNA of the *L. fermentum* CIP 102980T strain. The transforming clones selected proved to propagate a plasmid the inserts of which, having similar restriction profiles, controlled a Class II N-deoxyribosyltransferase activity. The sequence of one of these inserts developed a gene specifying a polypeptide of 168 amino acids with a molecular weight of 18878.20 Daltons having a similarity of 32.9% with the NTD polypeptide of *L. leichmanii* and 36.7% with the PTD polypeptide of *L. helveticus*. The sequence of this gene deviates from that of the ntd and ptd genes which makes them impossible to hybridize. The NTD polypeptide of *L. fermentum* has a more marked evolutive relationship for the enzyme of Class I (PTD of *L. helveticus*) and a functional affinity to Class II, suggesting an early evolutive divergence in the evolution of these enzymes. Its enzymatic activity could prove to be different to those of other species and be suitable for the preparation of a very large spectrum of nucleosides.

5. Inverse PCR Cloning of Four NTD Genes

Using degenerated oligonucleotides starting from regions of the amino acid sequence of the NTD polypeptide of *L. leichmanii* (Hück, 1997) an internal fragment on the ntd gene of *L. helveticus* was amplified. Starting from this fragment, oligonucleotides were synthesized so as to obtain all the gene by inverse PCR.

Starting from the two ntd sequences of *L. leichmannii* and *L. helveticus*, we redefined the consensus primers by isolating the ntd genes from other species of *lactobacilli* such as *L. acidophilus, L. crispatus, L. amylovorus* with the same result as that described above.

6. A Nutritional Screening to Distinguish the Two Activities of Deoxyribosyltransferase I and II To distinguish between the two deoxyribosyltransferase activities, the plasmidic DNA of different selected colonies was extracted then used to transform the auxotrophic PAK 26 strain for guanine and thymidine. In the PAK 26 strain, the dTMP cannot be synthesized starting from dUMP because the thymidylate synthase encoded by the thyA gene has been deactivated. Moreover, the thymine cannot be a source of thymidine because the thymidine phosphorylase encoded by the deoA gene and uridine phosphorylase encoded by the udp gene have been deleted. Deoxyguanosine (dR-G) and thymine (T) will be the sources of guanine and thymidine only if an N-deoxyribosyltransferase II activity is expressed in the PAK 26 strain to catalyze the exchange reaction dG+T⇌dT+G. Only the colonies expressing an N-deoxyribosyltransferase II activity can grow on a mineral glucose medium supplemented by deoxyguanosine and thymine as sources of guanine and thymidine. This second screening for example allowed the N-deoxyribosyltransferase II (ntd) activity to be correlated with the pLH2 plasmid containing the polynucleotide of SEQ ID No. 1 and coding for the ntd enzyme of *lactobacillus helveticus* and the N-deoxyribosyltransferase I (ptd) activity with the pLH4 plasmid containing the polynucleotide of SEQ ID No. 3 and coding for the ptd enzyme of *lactobacillus helveticus*.

TABLE 1

Growth of the PAK 6 strain expressing or not
expressing an N-deoxyribosyltransferase activity on a
glucose mineral medium (in vivo) and enzymatic activity
of corresponding raw extracts (in vitro)

|  | in vivo | | | in vitro | | | |
|---|---|---|---|---|---|---|---|
|  | A | G | dG | dG + A | dC + T | dG + A | dC + A |
| PAK 6 pSU19 | − | + | ± | − | − | − | − |
| ntd 6 PAK L1 | − | + | ± | + | + | + | + |
| ntd 6 PAK Lh | − | + | ± | + | + | + | + |
| ptd 6 PAK Lh | − | + | ± | + | − | + | − |
| ntd 6 PAK | − | + | ± | + | + | + | + |

(+) growth
(−) absence of growth
PAK 6: MG1655 ΔguaBA::Apra, Δdeo
ntd L1: gene coding for the N-deoxyribosyltransferase of *Lactobacillus leichmannii*
ntd Lh: gene coding for the N-deoxyribosyltransferase of *Lactobacillus helveticus*
ntd Lf: gene coding for the N-deoxyribosyltransferase of *Lactobacillus fermentum*
ptd Lh: gene coding for the purine deoxyribosyltransferase of *Lactobacillus helveticus*
A: adenine; G: guanine; T: thymine; dG: deoxyguanosine; dC: deoxycytidine

REFERENCES

Cadwell et al. (1992) Research 2: 28-33.
Carson & Wasson (1988) Biochem. Biophys. Res. Comm. 155, 829-834.
Carson et al., (1990) Proc. Natl. Acad. Sci. USA 81, 2232-2236.
Carter (1993) Curr. Op. Biotechnology 3, 533.
Danzin & Cardinaud (1976) Eur. J. Biochem. 62, 365-372.
Duck et al. (1990), Biotechniques, 9, 142.
Epstein (1992) Médecine/Sciences, 8, 902.
Fischer et al., (1990) Ger. Offen. DE 3840160.
Guatelli et al. (1990), Proc. Natl. Acad. Sci. USA 87: 1874.
Isono (1988) J. Antibiotics 12, 1711-1739.
Kievitis et al., (1991) J. Virol. Methods, 35, 273.
Köhler et Milstein. (1975) Nature 256, 495.
Krenitsky et al., (1981) Biochemistry 20, 3615-3621.
Kwoh et al. (1989) *Proc. Natl. Acad. Sci. USA*, 86, 1173.
Landegren et al. (1988) Science 241, 1077.
Matthews et al. (1988) Anal. Biochem., 169, 1-25.
Miele et al., (1983) J. Mol. Biol., 171, 281-285.
Neddleman et Wunsch (1970) J. Mol. Biol. 48: 443
Pearson et Lipman (1988) Proc. Natl. Acad. Sci. USA 85: 2444
Périgaud et al., (1992) Annales de l'Institut Pasteur Actualités 3, 179-215.
Perricaudet et al. (1992), La Recherche 23: 471.
Rolfs, A. et al. (1991), Berlin: Springer-Verlag.
Sambrook et al. (1989) Molecular cloning: a laboratory manual second edition—Cold Spring Harbor Laboratory Press. Cold Spring Harbor, N.Y. USA
Segev, (1992), Kessler C. Springer Verlag, Berlin, N.Y., 197-205.
Smith et Waterman (1981) Ad. App. Math. 2: 482
Temin, (1986) Retrovirus vectors for gene transfer. In Kucherlapati R., ed. Gene Transfer.
Walker et al. (1992) EMBO J. 1: 945-951
Wilson et al. (1995) Synthesis 1465-1479.
Wong C. H. et al. (1995) Angew. Chem. Int. Ed. Engl. 34, 412-432 and 521-546.

The invention claimed is:

1. An isolated polypeptide comprising an amino acid sequence that is at least 95% identical to SEQ ID NO.2, wherein said isolated polypeptide has the same N-deoxyribosyltransferase class II activity as that of the amino-acid sequence consisting of SEQ ID NO.2.

2. An isolated polypeptide comprising an amino acid sequence that is at least 95% identical to SEQ ID NO.2, wherein said isolated polypeptide displays a deoxyribosyltransferase class II activity able to carry out the exchange dR-G+A→dR-A+G.

3. An isolated polypeptide comprising an amino acid sequence that is at least 95% identical to SEQ ID NO.2, wherein said isolated polypeptide fulfils the guanine requirement of the E. coli PAK6 strain auxotrophic for guanine when said polypeptide is expressed in said strain.

4. An isolated polypeptide comprising the amino acid sequence SEQ ID NO.2.

5. An isolated polypeptide consisting of the amino-acid sequence SEQ ID NO.2.

6. An isolated polypeptide consisting of a fragment of the amino-acid sequence SEQ ID NO.2, wherein said isolated polypeptide has the same N-deoxyribosyltransferase class II activity as the amino-acid sequence consisting of SEQ ID NO.2.

7. An isolated polypeptide consisting of a fragment of the amino-acid sequence SEQ ID NO.2, wherein said isolated polypeptide displays a deoxyribosyltransferase class II activity able to carry out the exchange dR-G+A→dR-A+G.

8. An isolated polypeptide consisting of a fragment of the amino-acid sequence SEQ ID NO.2, wherein said isolated polypeptide fulfils the guanine requirement of the E. coli PAK6 strain auxotrophic for guanine when said polypeptide is expressed in said strain.

9. A recombinant polypeptide capable of being obtained by the expression of pLH2 vector comprising SEQ ID NO.1 in an appropriate host cell.

* * * * *

SEQUENCE LISTING

```
<160> NUMBER OF SEQ IDS NOS: 16

<210> SEQ ID NO 1
<211> LENGTH: 477
<212> TYPE: DNA
<213> ORGANISM: Lactobacillus helveticus NTD
<220> FEATURE:
<221> NAME/KEY: CDS
<222> LOCATION: (1)..(477)

<400> SEQUENCE: 1 atg aac aag aaa aag act tta tat ttt ggt gcc ggt tgg ttt aat gaa      48
Met Asn Lys Lys Lys Thr Leu Tyr Phe Gly Ala Gly Trp Phe Asn Glu
1               5                   10                  15 aag caa aac aaa gct tac aaa gaa gca atg gca gct tta aaa gaa aat      96
Lys Gln Asn Lys Ala Tyr Lys Glu Ala Met Ala Ala Leu Lys Glu Asn
                20                  25                  30 cca aca gtt gat tta gaa aat agt tat gtg ccc ctt gaa aac caa tac     144
Pro Thr Val Asp Leu Glu Asn Ser Tyr Val Pro Leu Glu Asn Gln Tyr
            35                  40                  45 aag ggt att cgc att gat gaa cat cca gaa tac ttg cac aac att gaa     192
Lys Gly Ile Arg Ile Asp Glu His Pro Glu Tyr Leu His Asn Ile Glu
        50                  55                  60 tgg gct tct gca acc tac cac aat gat tta gta gga att aag act tct     240
Trp Ala Ser Ala Thr Tyr His Asn Asp Leu Val Gly Ile Lys Thr Ser
65                  70                  75                  80
```

```
gat gtc atg ctt ggc gta tat ttg cca gaa gaa gaa gac gtc ggc tta    288
Asp Val Met Leu Gly Val Tyr Leu Pro Glu Glu Glu Asp Val Gly Leu
            85                  90                  95 ggc atg gaa ctg ggc tac gca tta tct caa gga aaa tat att tta ttg    336
Gly Met Glu Leu Gly Tyr Ala Leu Ser Gln Gly Lys Tyr Ile Leu Leu
        100                 105                 110 gtt atc cca gat gaa gat tac ggc aag cca atc aac tta atg agc tgg    384
Val Ile Pro Asp Glu Asp Tyr Gly Lys Pro Ile Asn Leu Met Ser Trp
    115                 120                 125 ggc gtt tgt gac aat gcc atc aag atc agt gaa tta aaa gac ttc gac    432
Gly Val Cys Asp Asn Ala Ile Lys Ile Ser Glu Leu Lys Asp Phe Asp
130                 135                 140 ttt aac aag cct cgc tac aat ttc tac gac gga gct gta tat taa       477
Phe Asn Lys Pro Arg Tyr Asn Phe Tyr Asp Gly Ala Val Tyr
145                 150                 155

<210> SEQ ID NO 2
<211> LENGTH: 158
<212> TYPE: PRT
<213> ORGANISM: Lactobacillus helveticus NTD

<400> SEQUENCE: 2

Met Asn Lys Lys Lys Thr Leu Tyr Phe Gly Ala Gly Trp Phe Asn Glu
1               5                   10                  15

Lys Gln Asn Lys Ala Tyr Lys Glu Ala Met Ala Ala Leu Lys Glu Asn
            20                  25                  30

Pro Thr Val Asp Leu Glu Asn Ser Tyr Val Pro Leu Glu Asn Gln Tyr
        35                  40                  45

Lys Gly Ile Arg Ile Asp Glu His Pro Glu Tyr Leu His Asn Ile Glu
    50                  55                  60

Trp Ala Ser Ala Thr Tyr His Asn Asp Leu Val Gly Ile Lys Thr Ser
65                  70                  75                  80

Asp Val Met Leu Gly Val Tyr Leu Pro Glu Glu Glu Asp Val Gly Leu
            85                  90                  95

Gly Met Glu Leu Gly Tyr Ala Leu Ser Gln Gly Lys Tyr Ile Leu Leu
        100                 105                 110

Val Ile Pro Asp Glu Asp Tyr Gly Lys Pro Ile Asn Leu Met Ser Trp
    115                 120                 125

Gly Val Cys Asp Asn Ala Ile Lys Ile Ser Glu Leu Lys Asp Phe Asp
130                 135                 140

Phe Asn Lys Pro Arg Tyr Asn Phe Tyr Asp Gly Ala Val Tyr
145                 150                 155

<210> SEQ ID NO 3
<211> LENGTH: 504
<212> TYPE: DNA
<213> ORGANISM: Lactobacillus helveticus PTD
<220> FEATURE:
<221> NAME/KEY: CDS
<222> LOCATION: (1)..(504)

<400> SEQUENCE: 3 atg aaa gca gta gtt cca aca gga aaa att tat tta ggc tca cca ttt    48
Met Lys Ala Val Val Pro Thr Gly Lys Ile Tyr Leu Gly Ser Pro Phe
1               5                   10                  15 tac agc gat gct caa aga gaa aga gca gct aag gca aaa gag ttg tta    96
Tyr Ser Asp Ala Gln Arg Glu Arg Ala Ala Lys Ala Lys Glu Leu Leu
            20                  25                  30 gca aaa aat cta agc atc gcg cac gtc ttc ttc ccc ttt gat gat ggt    144
```

```
Ala Lys Asn Leu Ser Ile Ala His Val Phe Phe Pro Phe Asp Asp Gly
            35                  40                  45 ttc acc gat cct gat gaa aag aat cct gaa att ggc ggc atc aga agc      192
Phe Thr Asp Pro Asp Glu Lys Asn Pro Glu Ile Gly Gly Ile Arg Ser
 50                  55                  60 atg gtt tgg cgg gat gca act tac caa aat gat tta act ggt att tcg      240
Met Val Trp Arg Asp Ala Thr Tyr Gln Asn Asp Leu Thr Gly Ile Ser
 65                  70                  75                  80 aat gcc act tgt ggc gtc ttc tta tat gat atg gat caa tta gat gac      288
Asn Ala Thr Cys Gly Val Phe Leu Tyr Asp Met Asp Gln Leu Asp Asp
                 85                  90                  95 ggc tct gcc ttt gaa att ggc ttc atg cgt gcg atg cat aag ccg gtg      336
Gly Ser Ala Phe Glu Ile Gly Phe Met Arg Ala Met His Lys Pro Val
            100                 105                 110 atc ttg gtg cca ttc act gag cat ccc gaa aaa gaa aag aaa atg aac      384
Ile Leu Val Pro Phe Thr Glu His Pro Glu Lys Glu Lys Lys Met Asn
        115                 120                 125 ctg atg atc gca caa ggc gta acc acc atc att gat ggc aat act gaa      432
Leu Met Ile Ala Gln Gly Val Thr Thr Ile Ile Asp Gly Asn Thr Glu
130                 135                 140 ttt gaa aaa cta gct gat tat aac ttc aac gaa tgt cct ttt aat cca      480
Phe Glu Lys Leu Ala Asp Tyr Asn Phe Asn Glu Cys Pro Phe Asn Pro
145                 150                 155                 160 gtt cgc ggt tac ggt atc tat taa                                      504
Val Arg Gly Tyr Gly Ile Tyr
                165

<210> SEQ ID NO 4
<211> LENGTH: 167
<212> TYPE: PRT
<213> ORGANISM: Lactobacillus helveticus PTD

<400> SEQUENCE: 4

Met Lys Ala Val Val Pro Thr Gly Lys Ile Tyr Leu Gly Ser Pro Phe
 1               5                  10                  15

Tyr Ser Asp Ala Gln Arg Glu Arg Ala Ala Lys Ala Lys Glu Leu Leu
            20                  25                  30

Ala Lys Asn Leu Ser Ile Ala His Val Phe Phe Pro Phe Asp Asp Gly
        35                  40                  45

Phe Thr Asp Pro Asp Glu Lys Asn Pro Glu Ile Gly Gly Ile Arg Ser
 50                  55                  60

Met Val Trp Arg Asp Ala Thr Tyr Gln Asn Asp Leu Thr Gly Ile Ser
 65                  70                  75                  80

Asn Ala Thr Cys Gly Val Phe Leu Tyr Asp Met Asp Gln Leu Asp Asp
                 85                  90                  95

Gly Ser Ala Phe Glu Ile Gly Phe Met Arg Ala Met His Lys Pro Val
            100                 105                 110

Ile Leu Val Pro Phe Thr Glu His Pro Glu Lys Glu Lys Lys Met Asn
        115                 120                 125

Leu Met Ile Ala Gln Gly Val Thr Thr Ile Ile Asp Gly Asn Thr Glu
130                 135                 140

Phe Glu Lys Leu Ala Asp Tyr Asn Phe Asn Glu Cys Pro Phe Asn Pro
145                 150                 155                 160

Val Arg Gly Tyr Gly Ile Tyr
                165

<210> SEQ ID NO 5
<211> LENGTH: 516
```

```
<212> TYPE: DNA
<213> ORGANISM: Lactobacillus fermentum NTD
<220> FEATURE:
<221> NAME/KEY: CDS
<222> LOCATION: (1)..(504)

<400> SEQUENCE: 5 ttg aaa aat acc gac cca gtt gct aac act aaa att tac ctg gct acc        48
Leu Lys Asn Thr Asp Pro Val Ala Asn Thr Lys Ile Tyr Leu Ala Thr
1               5                   10                  15 agc ttc ttc aac gaa gaa caa cgt gcc cgc atc cct caa gct cta gcc        96
Ser Phe Phe Asn Glu Glu Gln Arg Ala Arg Ile Pro Gln Ala Leu Ala
            20                  25                  30 caa cta gaa gcc aac ccg act gtc ggc gtt gtt cac cag cca ttc gat       144
Gln Leu Glu Ala Asn Pro Thr Val Gly Val Val His Gln Pro Phe Asp
        35                  40                  45 ttc caa tat aaa gat gca cgc gta gac tcc gat cct gcc ggc gtc ttt       192
Phe Gln Tyr Lys Asp Ala Arg Val Asp Ser Asp Pro Ala Gly Val Phe
    50                  55                  60 ggc agc ctc gaa tgg caa att gcc act tac aat aac gac ctc aac gcg       240
Gly Ser Leu Glu Trp Gln Ile Ala Thr Tyr Asn Asn Asp Leu Asn Ala
65                  70                  75                  80 gta gga act tcc gat gtc tgc gtt gct tta tac gat atg gac caa att       288
Val Gly Thr Ser Asp Val Cys Val Ala Leu Tyr Asp Met Asp Gln Ile
                85                  90                  95 gac gaa gga att tgt atg gaa atc ggc atg ttc gtc gcc ctc cat aaa       336
Asp Glu Gly Ile Cys Met Glu Ile Gly Met Phe Val Ala Leu His Lys
            100                 105                 110 cct atc gtt tta cta cct ttt act aag aaa gat aag tct gct tat gaa       384
Pro Ile Val Leu Leu Pro Phe Thr Lys Lys Asp Lys Ser Ala Tyr Glu
        115                 120                 125 gct aac cta atg cta gca cgg ggt gta act acc tgg ttg gaa cct aat       432
Ala Asn Leu Met Leu Ala Arg Gly Val Thr Thr Trp Leu Glu Pro Asn
    130                 135                 140 gac ttt agt ccc tta aaa gac ttt aac ttt aac cac cca atg gct caa       480
Asp Phe Ser Pro Leu Lys Asp Phe Asn Phe Asn His Pro Met Ala Gln
145                 150                 155                 160 cct ttc cca cca ttc aag gtt ttc taactaacct aa                         516
Pro Phe Pro Pro Phe Lys Val Phe
                165

<210> SEQ ID NO 6
<211> LENGTH: 168
<212> TYPE: PRT
<213> ORGANISM: Lactobacillus fermentum NTD

<400> SEQUENCE: 6

Leu Lys Asn Thr Asp Pro Val Ala Asn Thr Lys Ile Tyr Leu Ala Thr
1               5                   10                  15

Ser Phe Phe Asn Glu Glu Gln Arg Ala Arg Ile Pro Gln Ala Leu Ala
            20                  25                  30

Gln Leu Glu Ala Asn Pro Thr Val Gly Val Val His Gln Pro Phe Asp
        35                  40                  45

Phe Gln Tyr Lys Asp Ala Arg Val Asp Ser Asp Pro Ala Gly Val Phe
    50                  55                  60

Gly Ser Leu Glu Trp Gln Ile Ala Thr Tyr Asn Asn Asp Leu Asn Ala
65                  70                  75                  80

Val Gly Thr Ser Asp Val Cys Val Ala Leu Tyr Asp Met Asp Gln Ile
                85                  90                  95

Asp Glu Gly Ile Cys Met Glu Ile Gly Met Phe Val Ala Leu His Lys
```

```
                    100                 105                 110
Pro Ile Val Leu Leu Pro Phe Thr Lys Lys Asp Lys Ser Ala Tyr Glu
            115                 120                 125

Ala Asn Leu Met Leu Ala Arg Gly Val Thr Thr Trp Leu Glu Pro Asn
        130                 135                 140

Asp Phe Ser Pro Leu Lys Asp Phe Asn Phe Asn His Pro Met Ala Gln
145                 150                 155                 160

Pro Phe Pro Pro Phe Lys Val Phe
                165

<210> SEQ ID NO 7
<211> LENGTH: 255
<212> TYPE: DNA
<213> ORGANISM: Lactobacillus crispatus
<220> FEATURE:
<221> NAME/KEY: CDS
<222> LOCATION: (3)..(254)

<400> SEQUENCE: 7 ac aac cag tac aag ggt atc cgc gtt gat gaa cac cct gaa tac ttg        47
   Asn Gln Tyr Lys Gly Ile Arg Val Asp Glu His Pro Glu Tyr Leu
    1               5                   10                  15 cac gac att gaa tgg gca tca gct acc tac cat aac gac tta gta ggg        95
His Asp Ile Glu Trp Ala Ser Ala Thr Tyr His Asn Asp Leu Val Gly
                20                  25                  30 att aag tcc agc gac atc atg ctt ggc gtt tac ttg cct gaa gaa gaa       143
Ile Lys Ser Ser Asp Ile Met Leu Gly Val Tyr Leu Pro Glu Glu Glu
            35                  40                  45 gat gtt ggt ctg gga atg gaa ctt ggc tat gcc ctt tca aaa ggc aag       191
Asp Val Gly Leu Gly Met Glu Leu Gly Tyr Ala Leu Ser Lys Gly Lys
        50                  55                  60 tac atc ttg ttg gta att cct gat gaa gat tac ggt aag cca atc aac       239
Tyr Ile Leu Leu Val Ile Pro Asp Glu Asp Tyr Gly Lys Pro Ile Asn
    65                  70                  75 tta atg agc tgg ggc a                                                  255
Leu Met Ser Trp Gly
80

<210> SEQ ID NO 8
<211> LENGTH: 84
<212> TYPE: PRT
<213> ORGANISM: Lactobacillus crispatus

<400> SEQUENCE: 8

Asn Gln Tyr Lys Gly Ile Arg Val Asp Glu His Pro Glu Tyr Leu His
1               5                   10                  15

Asp Ile Glu Trp Ala Ser Ala Thr Tyr His Asn Asp Leu Val Gly Ile
            20                  25                  30

Lys Ser Ser Asp Ile Met Leu Gly Val Tyr Leu Pro Glu Glu Glu Asp
        35                  40                  45

Val Gly Leu Gly Met Glu Leu Gly Tyr Ala Leu Ser Lys Gly Lys Tyr
    50                  55                  60

Ile Leu Leu Val Ile Pro Asp Glu Asp Tyr Gly Lys Pro Ile Asn Leu
65                  70                  75                  80

Met Ser Trp Gly

<210> SEQ ID NO 9
<211> LENGTH: 399
<212> TYPE: DNA
<213> ORGANISM: Lactobacillus amylovorus NTD
```

```
<220> FEATURE:
<221> NAME/KEY: CDS
<222> LOCATION: (1)..(399)

<400> SEQUENCE: 9 atg gaa gct tta aag aag aac cct act gtt gac tta gaa aac agt tac       48
Met Glu Ala Leu Lys Lys Asn Pro Thr Val Asp Leu Glu Asn Ser Tyr
1               5                   10                  15 gtc cca ctt gat aac caa tac aaa ggc atc cgc gtt gat gaa cac cca       96
Val Pro Leu Asp Asn Gln Tyr Lys Gly Ile Arg Val Asp Glu His Pro
            20                  25                  30 gaa tat tta cac gac att gaa tgg gca tca tct acc tac cac aat gac      144
Glu Tyr Leu His Asp Ile Glu Trp Ala Ser Ser Thr Tyr His Asn Asp
        35                  40                  45 tta gtt ggt att aag tct tca gac gta atg ctc ggt gtt tat tta cct      192
Leu Val Gly Ile Lys Ser Ser Asp Val Met Leu Gly Val Tyr Leu Pro
    50                  55                  60 gaa gaa gaa gat gtt ggc ctt ggg atg gaa ctt ggc tac gca ttg tct      240
Glu Glu Glu Asp Val Gly Leu Gly Met Glu Leu Gly Tyr Ala Leu Ser
65                  70                  75                  80 caa ggt aaa tac atc ttg ctt gtc atc cct gac gaa gac tat ggt aag      288
Gln Gly Lys Tyr Ile Leu Leu Val Ile Pro Asp Glu Asp Tyr Gly Lys
                85                  90                  95 cca atc aac ttg atg agc tgg ggc gtt tgc gac aac gta atc aag atc      336
Pro Ile Asn Leu Met Ser Trp Gly Val Cys Asp Asn Val Ile Lys Ile
            100                 105                 110 agc gaa ttg aaa gac ttc gac ttt aac aga cct cgc ttc aac ttt tac      384
Ser Glu Leu Lys Asp Phe Asp Phe Asn Arg Pro Arg Phe Asn Phe Tyr
        115                 120                 125 gat ggt gct gtc tat                                                  399
Asp Gly Ala Val Tyr
    130

<210> SEQ ID NO 10
<211> LENGTH: 133
<212> TYPE: PRT
<213> ORGANISM: Lactobacillus amylovorus NTD

<400> SEQUENCE: 10

Met Glu Ala Leu Lys Lys Asn Pro Thr Val Asp Leu Glu Asn Ser Tyr
1               5                   10                  15

Val Pro Leu Asp Asn Gln Tyr Lys Gly Ile Arg Val Asp Glu His Pro
            20                  25                  30

Glu Tyr Leu His Asp Ile Glu Trp Ala Ser Ser Thr Tyr His Asn Asp
        35                  40                  45

Leu Val Gly Ile Lys Ser Ser Asp Val Met Leu Gly Val Tyr Leu Pro
    50                  55                  60

Glu Glu Glu Asp Val Gly Leu Gly Met Glu Leu Gly Tyr Ala Leu Ser
65                  70                  75                  80

Gln Gly Lys Tyr Ile Leu Leu Val Ile Pro Asp Glu Asp Tyr Gly Lys
                85                  90                  95

Pro Ile Asn Leu Met Ser Trp Gly Val Cys Asp Asn Val Ile Lys Ile
            100                 105                 110

Ser Glu Leu Lys Asp Phe Asp Phe Asn Arg Pro Arg Phe Asn Phe Tyr
        115                 120                 125

Asp Gly Ala Val Tyr
    130

<210> SEQ ID NO 11
```

<211> LENGTH: 480
<212> TYPE: DNA
<213> ORGANISM: Lactobacillus acidophillus NTD
<220> FEATURE:
<221> NAME/KEY: CDS
<222> LOCATION: (1)..(480)

<400> SEQUENCE: 11

```
atg atg gca aaa aca aaa act tta tat ttc ggc gct ggt tgg ttt aat        48
Met Met Ala Lys Thr Lys Thr Leu Tyr Phe Gly Ala Gly Trp Phe Asn
1               5                   10                  15 gaa aag caa aat aag gct tat aaa gca gct atg gaa gct tta aaa caa        96
Glu Lys Gln Asn Lys Ala Tyr Lys Ala Ala Met Glu Ala Leu Lys Gln
                20                  25                  30 aac cct act gtt gat ttg gaa aat agt tat gtt cca ctt gaa aat caa       144
Asn Pro Thr Val Asp Leu Glu Asn Ser Tyr Val Pro Leu Glu Asn Gln
            35                  40                  45 tat aaa gat att cgt gtt gat gaa cat cct gaa tac tta cac gac att       192
Tyr Lys Asp Ile Arg Val Asp Glu His Pro Glu Tyr Leu His Asp Ile
        50                  55                  60 gaa tgg gca tct gct act tat cac aac gac tta att ggt atc aaa tct       240
Glu Trp Ala Ser Ala Thr Tyr His Asn Asp Leu Ile Gly Ile Lys Ser
65                  70                  75                  80 tca gat att atg tta ggg gtt tac tta cct gaa gaa gaa gat gtt ggt       288
Ser Asp Ile Met Leu Gly Val Tyr Leu Pro Glu Glu Glu Asp Val Gly
                85                  90                  95 ctt ggt atg gaa ctt ggc tac gca tta tca caa ggc aaa tat atc tta       336
Leu Gly Met Glu Leu Gly Tyr Ala Leu Ser Gln Gly Lys Tyr Ile Leu
                100                 105                 110 ctc gtt att cct gac gaa gat tat ggc aag cct atc aac ttg atg agt       384
Leu Val Ile Pro Asp Glu Asp Tyr Gly Lys Pro Ile Asn Leu Met Ser
            115                 120                 125 tgg ggt gta tgt gat aac gct att aag atc agc gaa ttg aag gac ttc       432
Trp Gly Val Cys Asp Asn Ala Ile Lys Ile Ser Glu Leu Lys Asp Phe
        130                 135                 140 gac ttc aat aag cca cgc ttt aac ttc tat gat ggc gct gta tat taa       480
Asp Phe Asn Lys Pro Arg Phe Asn Phe Tyr Asp Gly Ala Val Tyr
145                 150                 155
```

<210> SEQ ID NO 12
<211> LENGTH: 159
<212> TYPE: PRT
<213> ORGANISM: Lactobacillus acidophillus NTD

<400> SEQUENCE: 12

```
Met Met Ala Lys Thr Lys Thr Leu Tyr Phe Gly Ala Gly Trp Phe Asn
1               5                   10                  15

Glu Lys Gln Asn Lys Ala Tyr Lys Ala Ala Met Glu Ala Leu Lys Gln
                20                  25                  30

Asn Pro Thr Val Asp Leu Glu Asn Ser Tyr Val Pro Leu Glu Asn Gln
            35                  40                  45

Tyr Lys Asp Ile Arg Val Asp Glu His Pro Glu Tyr Leu His Asp Ile
        50                  55                  60

Glu Trp Ala Ser Ala Thr Tyr His Asn Asp Leu Ile Gly Ile Lys Ser
65                  70                  75                  80

Ser Asp Ile Met Leu Gly Val Tyr Leu Pro Glu Glu Glu Asp Val Gly
                85                  90                  95

Leu Gly Met Glu Leu Gly Tyr Ala Leu Ser Gln Gly Lys Tyr Ile Leu
                100                 105                 110

Leu Val Ile Pro Asp Glu Asp Tyr Gly Lys Pro Ile Asn Leu Met Ser
```

```
                 115                 120                 125
Trp Gly Val Cys Asp Asn Ala Ile Lys Ile Ser Glu Leu Lys Asp Phe
    130                 135                 140

Asp Phe Asn Lys Pro Arg Phe Asn Phe Tyr Asp Gly Ala Val Tyr
145                 150                 155

<210> SEQ ID NO 13
<211> LENGTH: 795
<212> TYPE: DNA
<213> ORGANISM: Lactobacillus helveticus NTD
<220> FEATURE:
<221> NAME/KEY: misc_feature
<222> LOCATION: (133)..(133)
<223> OTHER INFORMATION: n means any nucleotide : a, g, c or t/u
<220> FEATURE:
<221> NAME/KEY: CDS
<222> LOCATION: (140)..(616)

<400> SEQUENCE: 13
aaaaaaattt tcagtattag tcattgaatt ttaccttcca ttatggaatt actattttta      60
gcgtaagtta acaagacgtt ttttcaatc gaaatatgt taagttaat tcgtcagcaa       120 tttttatggg ganaaaatt atg aac aag aaa aag act tta tat ttt ggt gcc     172
                      Met Asn Lys Lys Lys Thr Leu Tyr Phe Gly Ala
                        1               5                   10 ggt tgg ttt aat gaa aag caa aac aaa gct tac aaa gaa gca atg gca     220
Gly Trp Phe Asn Glu Lys Gln Asn Lys Ala Tyr Lys Glu Ala Met Ala
           15                  20                  25 gct tta aaa gaa aat cca aca gtt gat tta gaa aat agt tat gtg ccc     268
Ala Leu Lys Glu Asn Pro Thr Val Asp Leu Glu Asn Ser Tyr Val Pro
       30                  35                  40 ctt gaa aac caa tac aag ggt att cgc att gat gaa cat cca gaa tac     316
Leu Glu Asn Gln Tyr Lys Gly Ile Arg Ile Asp Glu His Pro Glu Tyr
   45                  50                  55 ttg cac aac att gaa tgg gct tct gca acc tac cac aat gat tta gta     364
Leu His Asn Ile Glu Trp Ala Ser Ala Thr Tyr His Asn Asp Leu Val
60                  65                  70                  75 gga att aag act tct gat gtc atg ctt ggc gta tat ttg cca gaa gaa     412
Gly Ile Lys Thr Ser Asp Val Met Leu Gly Val Tyr Leu Pro Glu Glu
                80                  85                  90 gaa gac gtc ggc tta ggc atg gaa ctg ggc tac gca tta tct caa gga     460
Glu Asp Val Gly Leu Gly Met Glu Leu Gly Tyr Ala Leu Ser Gln Gly
            95                 100                 105 aaa tat att tta ttg gtt atc cca gat gaa gat tac ggc aag cca atc     508
Lys Tyr Ile Leu Leu Val Ile Pro Asp Glu Asp Tyr Gly Lys Pro Ile
       110                 115                 120 aac tta atg agc tgg ggc gtt tgt gac aat gcc atc aag atc agt gaa     556
Asn Leu Met Ser Trp Gly Val Cys Asp Asn Ala Ile Lys Ile Ser Glu
   125                 130                 135 tta aaa gac ttc gac ttt aac aag cct cgc tac aat ttc tac gac gga     604
Leu Lys Asp Phe Asp Phe Asn Lys Pro Arg Tyr Asn Phe Tyr Asp Gly
140                 145                 150                 155 gct gta tat taa aaataagca aactaaatga cctatcgctt aaaaattgcg           656
Ala Val Tyr ataggtcatt ttttaatatt atctgtcatg tataaaatct ttcttaataa atatactcca    716
agtgattttc caaaaaaatt attattctat acccacttca tatggaagtc cgagtcactt    776
atgtaaatca tatatcact                                                  795

<210> SEQ ID NO 14
<211> LENGTH: 158
```

```
<212> TYPE: PRT
<213> ORGANISM: Lactobacillus helveticus NTD

<400> SEQUENCE: 14

Met Asn Lys Lys Lys Thr Leu Tyr Phe Gly Ala Gly Trp Phe Asn Glu
1               5                   10                  15

Lys Gln Asn Lys Ala Tyr Lys Glu Ala Met Ala Ala Leu Lys Glu Asn
            20                  25                  30

Pro Thr Val Asp Leu Glu Asn Ser Tyr Val Pro Leu Glu Asn Gln Tyr
        35                  40                  45

Lys Gly Ile Arg Ile Asp Glu His Pro Glu Tyr Leu His Asn Ile Glu
50                  55                  60

Trp Ala Ser Ala Thr Tyr His Asn Asp Leu Val Gly Ile Lys Thr Ser
65                  70                  75                  80

Asp Val Met Leu Gly Val Tyr Leu Pro Glu Glu Asp Val Gly Leu
                85                  90                  95

Gly Met Glu Leu Gly Tyr Ala Leu Ser Gln Gly Lys Tyr Ile Leu Leu
            100                 105                 110

Val Ile Pro Asp Glu Asp Tyr Gly Lys Pro Ile Asn Leu Met Ser Trp
        115                 120                 125

Gly Val Cys Asp Asn Ala Ile Lys Ile Ser Glu Leu Lys Asp Phe Asp
    130                 135                 140

Phe Asn Lys Pro Arg Tyr Asn Phe Tyr Asp Gly Ala Val Tyr
145                 150                 155

<210> SEQ ID NO 15
<211> LENGTH: 18
<212> TYPE: DNA
<213> ORGANISM: Lactobacillus leichmannii NTD1

<400> SEQUENCE: 15
agacgatcta cttcggtg                                                 18

<210> SEQ ID NO 16
<211> LENGTH: 18
<212> TYPE: DNA
<213> ORGANISM: Lactobacillus leichmannii NTD2

<400> SEQUENCE: 16
acggcacctt cgtagaag                                                 18
```